United States Patent
Nehra et al.

(12) 
(10) Patent No.: US 6,541,682 B1
(45) Date of Patent: *Apr. 1, 2003

(54) PLASTID TRANSFORMATION OF SOLANACEOUS PLANTS

(75) Inventors: Narender S. Nehra, Chesterfield, MO (US); David J. Schaaf, Davis, CA (US); Vladimir Sidorov, Chesterfield, MO (US); David M. Stalker, Woodland, CA (US); Guangning Ye, Ellisville, MO (US)

(73) Assignee: Calgene LLC, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/191,303

(22) Filed: Nov. 12, 1998

(51) Int. Cl.$^7$ .................. C12N 15/82; C12N 15/29; C12N 5/10; A01H 5/00; A01H 5/10

(52) U.S. Cl. .................. 800/278; 800/287; 800/288; 800/317; 800/317.2; 800/323.1; 435/417; 435/419; 435/429; 435/430; 435/468

(58) Field of Search .................. 800/278, 287, 800/288, 317, 317.2, 323.1; 435/468, 419, 417, 430, 429

(56) References Cited

U.S. PATENT DOCUMENTS

| | | | |
|---|---|---|---|
| 5,015,580 A | 5/1991 | Christou et al. | |
| 5,094,945 A | 3/1992 | Comai | |
| 5,349,123 A | 9/1994 | Shewmaker et al. | |
| 5,349,125 A | * 9/1994 | Holton et al. | 800/205 |
| 5,378,619 A | 1/1995 | Rogers | |
| 5,416,011 A | 5/1995 | Hinchee et al. | |
| 5,451,513 A | 9/1995 | Maliga et al. | |
| 5,545,818 A | 8/1996 | McBride | 800/205 |
| 5,576,198 A | 11/1996 | McBride et al. | |
| 5,627,061 A | 5/1997 | Barry et al. | |
| 5,633,435 A | 5/1997 | Barry et al. | |
| 5,693,507 A | 12/1997 | Daniell et al. | |

FOREIGN PATENT DOCUMENTS

| | | |
|---|---|---|
| GB | 2183660 A | 6/1987 |
| WO | WO 92/15675 | 9/1992 |
| WO | WO 99/10513 | 3/1999 |

OTHER PUBLICATIONS

Dix et al. Euphytica 85(1–3):29–34, 1995.*
Sidorov et al. Theor. Appl. Genet. 88(3–4): 525–529, 1994.*
Van Grinsven et al. pp. 859–866 In: Genetic Manip. Plant Breed., Horn, W., ed., 1986.*
Perl et al. Plant Mol. Biol. 19:815–823 (No. 5), 1992.*
Chasan, R. Plant Cell 4(1):1–2, Jan. 1992.*
McBride et al. Amplifications of a chimeric bacillus gene in chloroplasts leads to an extraordinary level of an insecticidal protein in tobacco. *Biotechnology* 13:362–365 (1995).
Sheen et al. Green–fluorescent protein as a new vital marker in plant cells. *The Plant Journal* 8(5):777–784 (1995).
Sidorov et al. Stable chloroplast transformation in potato: use of green fluorescent protein as a plastid marker. *The Plant Journal* 19(2):209–216 (1999).
Staub et al. High–yield production of a human therapeutic protein in tobacco chloroplasts. *Nature Biotechnology* 18:333–338 (2000).
Horsch, et al., "A simple and general method for transferring genes into plants" *Science* 227, 1229–1231 (1985).
Klein, et al., "Transformation of microbes, plants and animals by particle bombardment" *Bio/Technology* 10, 286–291 (1992).
Padgette, et al., "Bacterial expression and isolation of *Petunia hybrida* 5–enol–pyruvylshikimate–3–phosphate synthase" *Archives of Biochemistry and Biophysics* 258(2), 564–573 (1987).
Stalker, et al., "A single amino acid substitution in the enzyme 5–enolpyruvylshikimate–3–phosphate synthase confers resistance to the herbicide glyphosate" *The Journal of Biological Chemistry* 260(8), 4724–4728 (1985).
Stalker, et al., "Purification and properties of a nitrilase specific for the herbicide bromoxynil and corresponding nucleotide sequence analysis of the bxn gene" *The Journal of Biological Chemistry* 263(13), 6310–6314 (1988).
Penaloza–Vazquez, et al., "Expression of the hygromycin B phosphotransferase gene confers tolerance to the herbicide glyphosate" *Plant Cell Reports* 14, 482–487 (1995).
DeBlock et al., "Engineering herbicide resistance in plants by expression of a detoxifying enzyme" *The EMBO Journal* 6(9), 2513–1518 (1987).
Sathasivan, et al., "Nucleotide sequence of a mutant acetolactate synthase gene from an imidazolinone–resistant *Arabidopsis thaliana* var. Columbia" *Nucleic Acids Research* 18(8), 2188–2193 (1990).
Misawa, et al., "Expression of an Erwinia phytoene desaturase gene not only confers multiple resistance to herbicides interfering with carotenoid biosynthesis but also alters xanthophyll metabolism in transgenic plants" *The Plant Journal* 6(4), 481–489 (1994).

(List continued on next page.)

Primary Examiner—David T. Fox

(57) ABSTRACT

A method is provided for transforming solanaceous plants to express DNA sequences interest from the plant cell plastid. The improved method allows the transformation of solanaceous plant tissue which is not obtained from tobacco with DNA constructs. Such DNA constructs comprise, in the 5' to 3' direction of transcription, a promoter region functional in a plant plastid and a DNA sequence of interest. The method can be utilized in the transformation of solanaceous plants, such as potato and petunia. The invention further provides constructs and methods for the expression of green fluorescent protein from the plant cell plastid.

15 Claims, 8 Drawing Sheets

OTHER PUBLICATIONS

Misawa, et al., "Functional expression of the *Erwinia uredovora* carotenoid biosynthesis gene crtI in transgenic plants showing an increase of β–carotene biosynthesis activity and resistance to the bleaching herbicide norflurazon" *The Plant Journal* 4(5), 833–840 (1993).

Padgette, et al., *Herbicide–Resistant Crops*, Chapter 4, CRC Press, Inc., 53–88 (1996).

Gray, et al., "Reducing transgene escape routes" *Nature* 392, 653–654 (1998).

Goodman, et al., *Pharmacological Basis of Therapeutics, 8th edition*, Sectin XV, Pergaman Press 1332–1360 (1990).

Worrell, et al., "Expression of a maize sucrose phosphate synthase in tomato alters leaf carbohydrate partitioning" *The Plant Cell* 3, 1121–1130 (1991).

Klann, et al., "Tomato fruit acid invertase complementary DNA" *Plant Physiology* 99, 351–353 (1992).

Crameri, et al., "Improved green fluorescent protein by molecular evolution using DNA shuffling" *Nature Biotechnology* 14, 315–319 (1996).

Hood, et al., "The hypervirulences of *Agrbacterium tumefaciens* A281 is encoded in a region of pTiBo542 outside of T–DNA" *Journal of Bacteriology* 168(3), 1291–1301 (1986).

Holton, T., "Petal–specific gene expression in *Petunia hybrida*" PhD dissertation: The Russell Grimwade School of Biochemistry, University of Melbourne, 1–137 Mar. 1992.

Shinozaki, et al., "The complete nucleotide sequence of the tobacco chloroplast genome: its gene organization and expression" *The EMBO Journal* 5(9), 2043–2049 (1986).

Zoubenko, et al., "Efficient targeting of foreign genes into the tobacco plastid genome" *Nucleic Acids Research* 22(19), 3819–3824 (1994).

Sanford, et al., "Optimizing the biolistic process for different biological applications" *Methods in Enzymology* 217, 483–509 (1993).

Ye, et al., "Optimization of delivery of foreign DNA into higher–plant chloroplast" *Plant Molecular Biology* 15, 809–819 (1990).

Blowers, et al., "Studies on Chlamydomonas chloroplast transformation: Foreign DNA can be stably maintained in the chromosome" *The Plant Cell* 1, 123–132 (1989).

McBride, et al., "Controlled expression of plastid transgenes in plants based on a nuclear DNA–encoded and plastid–targeted T7 RNA polymerase" *Proceedings of the National Academy of Sciences of the USA* 91, 7301–7305 (1994).

Daniell, et al., "Foreign gene expression in chloroplasts of higher plants mediated by tungsten particle bombardment" *Methods in Enzymology* 217, 536–557 (1993).

Svab, et al., "High–frequency plastid transformation in tobacco by selection for a chimeric aadA gene" *Proceedings of the National Academy of Sciences of the USA* 90, 913–917 (1993).

Svab, et al., "Stable transformation of plastids in higher plants" *Proceedings of the National Academy of Sciences of the USA* 87, 8526–8530 (1990).

Staub, et al., "Accumulation of D1 polypeptide in tobacco plastids is regulated via the untranslated region of the psbA mRNA" *The EMBO Journal* 12(2), 601–606 (1993).

Daniell, et al., "Uptake and expression of bacterial and cyanobacterial genes by isolated cucumber etioplasts" *Proceedings of the National Academy of Sciences of the USA* 84, 6349–6353 (1987).

Herrera–Estrella, et al., "Expression of chimaeric genes transferred into plant cells using a Ti–plasmid–derived vector" *Nature* 303, 209–213 (1983).

DeBlock, et al., "Chloroplast transformation by *Agrobacterium tumefaciens*" *The EMBO Journal* 4(6), 1367–1372 (1985).

Herrera–Estrella, et al., "Light–inducible and chloroplast–associated expression of a chimaeric gene introduced into Nicotianatabacum using a Ti plasmid vector" *Nature* 310, 115–120 (1984).

Maliga, et al., "Towards plastid transformation in flowering plants" *Tibtech* 11, 101–107 (1993).

Boynton, et al., "Chloroplast transformation in Chlamydomonas with high velocity microprojectiles" *Science* 240, 1534–1538 (1988).

Sathasivan, et al., "Nucleotide sequence of a mutant acetolactate synthase gene from an imidazolinone–resistant *Arabidopsis thaliana* var. Columbia" *Nucleic Acids Research* 18(8), 2188 (1990).

Siemering, et al., "Mutations that suppress the thermosensitivity of green fluorescent protein" *Current Biology* 6(12), 1653–1663 (1996).

Salopek, et al., "Greening of non–transformed and *Agrobacterium rhizogenes* transformed adventitious potato roots" *Biologia (Bratislava)* 53(1), 127–132 (1998).

* cited by examiner

Chloroplast trans.
BamHI frag. probe
Xanthi & petunia "Mitchell"
3 day -70°C exp.

Chloroplast trans.
AADA probe
Blot from 2/5/96
1 day RT° exp

PLASTID TRANSFORMATION OF SOLANACEOUS PLANTS

TECHNICAL FIELD

The invention relates to methods of genetically transforming plant plastids, and more specifically to genetically transforming the plastid genomes of Solanaceous plant species.

BACKGROUND

The plastids of higher plants are an attractive target for genetic engineering. Plant plastids (chloroplasts, amyloplasts, elaioplasts, etioplasts, chromoplasts, etc.) are the major biosynthetic centers that, in addition to photosynthesis, are responsible for production of industrially important compounds such as amino acids, complex carbohydrates, fatty acids, and pigments. Plastids are derived from a common precursor known as a proplastid and thus the plastids present in a given plant species all have the same genetic content. In general, plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest which potentially can result in very high levels of foreign gene expression. In addition, plastids of most plants are maternally inherited. Consequently, unlike heterologous genes expressed in the nucleus, heterologous genes expressed in plastids are not pollen disseminated, therefore, a trait introduced into a plant plastid will not be transmitted to wild-type relatives.

Unfortunately, successful chloroplast transformation techniques described thusfar have been limited to tobacco (U.S. Pat. No. 5,451,513; Svab et. al. (1990), *Proc. Natl. Acad. Sci. USA* 87:8526–8530 and Svab et al. (1993), *Proc. Natl. Acad. Sci. USA* 90:913–197). For practical applications of genetic engineering techniques to crop plant plastids, chloroplast transformation techniques for a wide variety of crop plants are needed in the art.

The genus Solanaceae includes many agriculturally important plants, and includes some 95 genera. Solanaceous lid crop plants include potato, tomato, eggplant, and other lesser known edible fruits from Physalis (cape gooseberry, strawberry tomato, jamberberry, sugar cherry, chinese lantern, etc), tamarillo, and Capsicum (sweet and chili peppers). The genus also includes many cultivated ornamentals, for example, Petunia, Lycium, Solanum, and Solandra. Other important crops from the genus Solanaceae include tobacco (Nicotiana) and other poisonous alkaloid producing plants such as Hyoscyamus and Datura.

Plastids of higher plants present an attractive target for genetic engineering. As mentioned above, plastids of higher plants are maternally inherited. This offers an advantage for genetic engineering of plants for tolerance or resistance to natural or chemical conditions, such as herbicide tolerance, as these traits will not be transmitted to wild-type relatives.

The production of chloroplast transformation methods applicable to crop species other than tobacco is needed in the art. Such methods provide for a novel means of genetic engineering via plastid transformation to an attractive alternative to nuclear expression of agronomically as well as qualitatively important traits via genetic engineering of plant plastids.

Relevant Literature

Stable transformation of plastids has been reported in the green algae Chlamydomonas (Boynton et al. (1988) *Science* 240:1534–1538) and most recently in higher plants (Svab et al. (1990) *Proc. Natl. Acad. Sci. USA* 87:8526–8530; Svab and Maliga (1993) *Proc. Natl. Acad. Sci. USA* 90:913–917). These methods rely on particle gun delivery of DNA containing a selectable marker and targeting to the plastid genome by homologous recombination.

The complete DNA sequences of the plastid genomes from liverwort (Ohyama et al. (1986) *Nature* 322:572–574), rice (Hiratsuka et al. (1989) *Mol. Gen. Genet.* 217:185–194), and tobacco (Shinozaki et al. (1986) *EMBO J.* 5:2043–2049) have been reported.

SUMMARY OF THE INVENTION

The present invention provides methods for the transformation and regeneration of plants containing plant cells, the plastids of which have been stably transformed by a foreign DNA of interest. The method generally comprises transforming a Solanaceous plant cell plastid with a DNA construct; selecting for cells which contain the DNA construct; and obtaining a mature multicellular plant, the cells of which contain the DNA construct in the plant cell plastid.

The instant invention also provides methods for transforming the plastids of Solanaceous plant cells with a DNA construct generally comprising, in the 5' to 3' direction of transcription, a promoter region functional in a plant cell plastid, a DNA sequence of interest, and a transcription termination region functional in a plant cell plastid.

Furthermore, the present invention also provides the multicellular solanaceous plant obtained by the methods described herein.

The invention also provides a multicellular solanaceous plant, the plastids of which have been transformed with a DNA construct of interest.

The invention also provides a method for obtaining a plant cell, of which the plastid has been stably transformed with a DNA construct, comprising in the 5' to 3' direction of transcription, a promoter functional in a plant cell plastid, a DNA sequence encoding a green fluorescent protein (herein referred to as GFP), and a transcriptional termination region functional in a plant cell plastid.

The invention also provides for the multicellular plant, the plastids of which have been transformed with a DNA construct comprising in the 5' to 3' direction of transcription, a promoter functional in a plant cell plastid, a DNA sequence encoding a green fluorescent protein (herein referred to as GFP), and a transcriptional termination region functional in a plant cell plastid.

DETAILED DESCRIPTION OF THE INVENTION

Figure 1:
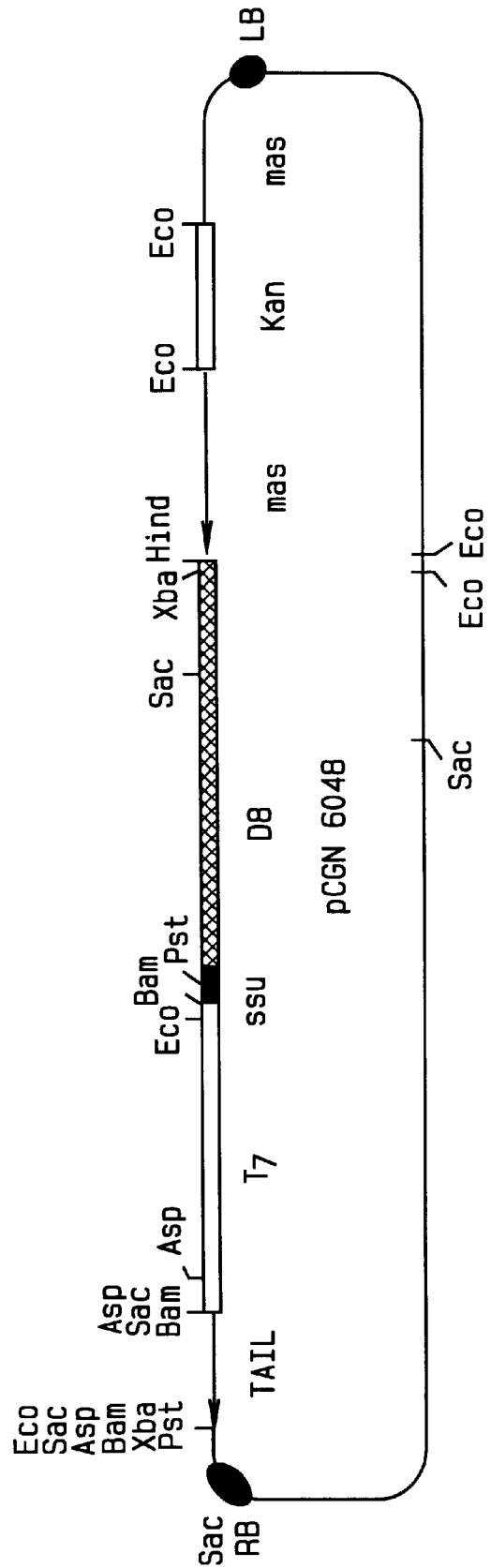
FIG. 1 provides a schematic representation of the plastid expression vector pCGN6048.

In accordance with the subject invention, methods are provided for obtaining plant cells containing chloroplasts into which heterologous DNA has been inserted. The method generally encompasses transforming a plant cell with plastid expression vectors. The plastid expression constructs generally contain nucleic acid sequences comprising, as operably linked components in the 5' to 3' direction of transcription, a promoter functional in a plant plastid, a DNA sequence of interest, and a transcription termination region capable of terminating transcription in a plant plastid.

Of particular interest in the present invention is the method of producing a plant cell from a Solanaceous plant species other than tobacco having integrated into it's chloroplast genome a DNA construct to direct the expression of a DNA sequence of interest from the plant cell plastid.

As described in more detail in the examples below, methods are provided for the transformation of Solanaceous plant species, exemplified by methods for potato and petunia transformation. The methods provided herein are used to produce transplastomic plants expressing DNA sequences of interest from the cell plastid.

The transformation methods generally comprise particle gun bombardment of microprojectiles carrying a DNA construct into plant cells of prepared leaf tissue samples. The bombarded leaf samples are cultured for approximately 1 to 3 days on cell division promoting media, then transferred to a media containing a selective agent, as well as the relevant hormones.

Thus, the methods described in the present invention provide novel methods for obtaining Solanaceous plants containing DNA constructs in the plant cell plastid. The novel methods are used to produce transplastomic plants from several Solanaceous plant genus', including important agricultural genus such as potato.

The plant cell used for transformation methods of the present invention may be obtained from any plant tissue source which contain plastids, and which has the ability to regenerate into a mature plant or structure which will give rise to a mature plant. Such tissues include but are not limited to; leaf tissue, cotyledons (including cotyledonary notch), hypocotyls, epicotyls, stem sections, embryogenic callus, callus, petioles, protoplasts, as well as some seeds and embryos. Furthermore, the tissue source may derived from plants grown in a variety of conditions, including in vitro, soil grown, and the like.

Typically, DNA constructs of interest are transformed into the plastids of a plant cell using particle gun bombardment. Stable transformation of tobacco plastid genomes by particle bombardment is reported (Svab et.al. (1990 supra) and Svab et al. (1993 supra)). The methods reported therein, may be employed in the transformation methods of the present invention. Other methods are known in the art, and are described by O'Neil, et al. (1993) Plant Journal 3:729–738 and Golds, et al. (1993) Bio/Technology 11:95–97, the entireties of which are incorporated herein by reference.

The regeneration of whole plants from a transformed cell contained in the tissue used in transformation involves several growth stages. Typically, a tissue, having been excised from an adult plant or germinated seedling, is placed in a chemically defined medium under sterile conditions. By growing the explant under such controlled conditions for a period of time, an undifferentiated mass of cells, referred to as a callus, may form.

By culturing this callus under the proper set of conditions, e.g., nutrients, light, temperature, humidity, and by providing the proper combination and concentration of plant growth regulators, the calli may be induced to form differentiated cells and regenerate plant shoots. Plant shoots, sometimes referred to as plantlets, containing meristem tissue are then transferred to a media for the induction of root production.

Generally, bombarded tissue is cultured for approximately 1 to 3 days on a cell division-promoting media, after which the plant tissue is transferred to a selective media containing an inhibitory amount of the particular selective agent, as well as the particular hormones and other substances necessary to obtain regeneration for that particular plant species. Shoots are then subcultured on the same selective media to ensure production and selection of homoplasmic shoots.

The selective media may be solid or liquid by the addition of a solidifying agent, such as agar. Liquid selective media allows for greater surface area of contact of the plant tissue with the selective media containing particular hormones, particular selective agent and other substances necessary to obtain regeneration.

The amount of selective agent may remain constant in the media during regeneration. Alternatively, the amount of selective agent may initially be at higher levels, then lowered during later stages of regeneration. Furthermore, the selective agent amount may be lower during the initial stages of regeneration, then increased later in regeneration.

Transplastomic plants are analyzed for a pure population of transformed plastid genomes (homoplasmic lines). Homoplasmy is verified using Southern analysis employing nucleic acid probes spanning a region of the transgene and chloroplast genome (i.e. the insertion region). Transplastomic plants which are heteroplasmic (i.e. contain a mixture of plastid genomes containing and lacking the transgene) are characterized by a hybridization pattern of wild type and transgenic bands. Homoplasmic plants show a hybridization pattern lacking the wild type band.

Alternatively, homoplasmy may be verified using the polymerase chain reaction (PCR). PCR primers are utilized which are targeted to amplify from sequences from the insertion region. For example, a pair of primers may be utilized in a PCR reaction. One primer amplifies from a region in the transgene, while the second primer amplifies from a region proximal to the insertion region towards the insertion region. A second PCR reaction is performed using primers designed to amplify the region of insertion. Transplastomic lines identified as homoplasmic produce the expected size fragment in the first reaction, while they do not produce the predicted size fragment in the second reaction.

As described in more detail in the examples below, transplastomic Solanaceous species, potato and petunia are produced from methods described herein.

Other Solanaceous plant species may be similarly transformed using related techniques. Suitable plants for the practice of the present invention include, but are not limited to, tomato, eggplant, Capsicum species, Physalis species, as well as ornamentals for example Solanum, Cestrum, Solandra, and Lycium.

Also of interest in the present invention is the use of novel reporter genes to facilitate the development of transplastomic plants.

Reporter genes used for the study of plastid transformation have been limited to the use of the GUS. Analysis techniques for the expression of GUS from transgenic tissues involves destruction of tissues prior to staining. Generally, the tissue is infiltrated with a glucoronide containing solution, then destained with an alcohol solution to remove chlorophyll background. The stained tissue is then visually observed for GUS staining, as evidenced by a blue coloration of the cells expressing β-glucoronidase.

As discussed in more detail in the examples that follow, constructs employing the green fluorescence protein (GFP) are used to transform Solanaceous plants such that the transformed Solanaceous plant has integrated into the chloroplast genome the construct to direct the expression of the GFP from the plastid. Cells of plants expressing GFP may be visualized under ultraviolet (uv) light, without the need for destructive methods. Visualized under uv light, the cells expressing GFP fluoresce as a green color. Mutations in the GFP coding sequence shift the excitation wavelength to blue light, allowing for a more convenient visualization of expression on a green plant surface.

Furthermore, transplastomic tobacco plants are identified which are homoplasmic for the DNA sequences of interest encoding the GFP gene. Homoplasmic plants demonstrate a high level of protein expression from the plastid. Transplastomic tobacco plants are obtained using the methods of the present invention to transform a DNA construct comprising a marker gene, such as GFP, expressed from a promoter sequence which is functional in a plant cell plastid.

In developing the constructs the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA which is employed in the regulatory regions or the DNA sequences of interest for expression in the plastids. Methods for restriction digests, Klenow blunt end treatments, ligations, and the like are well known to those in the art and are described, for example, by Maniatis et al. (in *Molecular cloning: a laboratory manual* (1989) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation of the DNA by joining or removing sequences, linkers, or the like.

Preferably, the vectors will be capable of replication to at least a relatively high copy number in *E. coli*. A number of vectors are readily available for cloning, including such vectors as pBR322, vectors of the pUC series, the M13 series vectors, and pBluescript vectors (Stratagene; La Jolla, Calif.).

In order to provide a means of selecting the desired plant cells, vectors for plastid transformation typically contain a construct which provides for expression of a selectable marker gene. Marker genes are plant-expressible DNA sequences which express a polypeptide which resists a natural inhibition by, attenuates, or inactivates a selective substance, i.e., antibiotic, herbicide etc.

Alternatively, a marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct.

Detection of the marker phenotype makes possible the selection of cells having a second gene to which the marker gene has been linked. This second gene typically comprises a desirable phenotype which is not readily identifiable in transformed cells, but which is present when the plant cell or derivative thereof is grown to maturity, even under conditions wherein the selectable marker phenotype itself is not apparent.

The use of such a marker for identification of plant cells containing a plastid construct has been described by Svab et al. (1993, supra). In the examples provided below, a bacterial aadA gene is expressed as the marker under the regulatory control of chloroplast 5' promoter and 3' transcription termination regions, specifically the regulatory regions of the psbA gene (described in Staub et al., *EMBO J.* (1993) 12(2): 601–606). Numerous additional promoter regions may also be used to drive expression of the selectable marker gene, including various plastid promoters and bacterial promoters which have been shown to function in plant plastids.

Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Cells which do not contain the selectable marker gene product are bleached. Selection for the aadA gene marker is thus based on identification of plant cells which are not bleached by the presence of streptomycin, or more preferably spectinomycin, in the plant growth medium.

A number of markers have been developed for use with plant cells, such as resistance to chloramphenicol, the aminoglycoside G418, hygromycin, or the like. Other genes which encode a product involved in chloroplast metabolism may also be used as selectable markers. For example, genes which provide resistance to plant herbicides such as glyphosate, bromoxynil or imidazolinone may find particular use. Such genes have been reported (Stalker et al., *J. Biol. Chem.* (1985) 260:4724–4728 (glyphosate resistant EPSP); Stalker et al., *J. Biol. Chem.* (1985) 263:6310–6314 (bromoxynil resistant nitrilase gene); and Sathasivan et al.,

*Nucl. Acids Res.* (1990) 18:2188 (AHAS imidazolinone resistance gene)).

The vectors for use in plastid transformation may include sequences to provide for an origin of replication to allow the introduced construct to replicate autonomously in the plastid. Such sequences are known in the art and are described in U.S. Pat. No. 5,693,507, the entirety of which is incorporated herein by reference.

The vectors for use in plastid transformation preferably include means for providing a stable transfer of the plastid expression construct and selectable marker construct into the plastid genome. This is most conveniently provided by regions of homology to the target plastid genome. The regions of homology flank the construct to be transferred and provide for transfer to the plastid genome by homologous recombination, via a double crossover into the genome. The complete DNA sequence of the plastid genome of tobacco has been reported (Shinozaki et al., *EMBO J.* (1986) 5:2043–2049). Complete DNA sequences of the plastid genomes from liverwort (Ohyama et al., *Nature* (1986) 322:572–574) and rice (Hiratsuka et al., *Mol. Gen. Genet.* (1989) 217:185–194), have also been reported.

Where the regions of homology are present in the inverted repeat regions of the plastid genome (known as IRA and IRB), two copies of the transgene are expected per transformed plastid. Where the regions of homology are present outside the inverted repeat regions of the plastid genome, one copy of the transgene is expected per transformed plastid. The regions of homology within the plastid genome are approximately 1 kb in size. Smaller regions of homology may also be used, and as little as 100 bp can provide for homologous recombination into the plastid genome. However, the frequency of recombination and thus the frequency of obtaining plants having transformed plastids decreases with decreasing size of the homology regions.

Examples of constructs having regions of homology the plastid genome are described in Svab et.al. (1990 supra), Svab et al. (1993 supra) and Zoubenko et al. (*Nuc Acid Res* (1994) 22(19):3819–3824).

Surprisingly, it has been found that homologous regions derived from the tobacco genome are capable of directing homologous recombination in a heterologous plastid genome. For example, as described in more detail in the examples that follow, homologous regions derived from the tobacco plastid 16S rDNA and rps7/12 sequences are used in constructs to transform the plastids of potato and petunia. These sequences are capable of directing the insertion of DNA sequence located between them into the plastid genome of potato and petunia.

However, to improve the transformation efficiency, regions of homology derived from the sequences of the plastid genome of the target plant genus may find use. Such regions of homology may be obtained by utilizing PCR reactions to isolate sequences corresponding to the regions of homology in the target plant genus (also referred to herein as a homologous plastid genome). Thus, as used herein, regions of homology to a homologous plastid genome refers to DNA sequences which are used in the preparation of constructs to direct the integration of the expression construct into the plastid genome of the same plant genus as that from which the regions are derived.

Expression constructs for use in the methods of the present invention find use in directing the expression of DNA sequences encoding genes involved in a wide variety of plant genetic engineering applications. Such genes may encode for proteins involved in agronomic traits (input traits) such as herbicide tolerance and disease resistance, or quality traits (output traits) such as fatty acid composition modification and carotenoid production. Furthermore, DNA sequences encoding for proteins for the production of human biologics in a plant cell plastid also find use in the expression constructs of the present invention.

As described in more detail in the examples below, constructs are prepared to direct the expression of a DNA sequence coding for an enzyme involved in the degradation of cellulose. The constructs described comprise DNA sequences encoding for green fluorescent proteins.

The skilled artisan will recognize that other DNA sequences find use in the constructs for use in the methods of the present invention.

For example, the expression constructs for use in the present invention allow for the high level expression of agronomically important traits such as herbicide and stress tolerance from a plant cell plastid. DNA sequences encoding for proteins involved in herbicide tolerance are known in the art, and include, but are not limited to DNA sequences encoding for 5-enolpyruvylshikimate-3-phosphate synthase (EPSPS, described in U.S. Pat. Nos. 5,627,061, and 5,633,435, Padgette et al. (1996) Herbicide Resistant Crops, Lewis Publishers, 53–85, and in Penaloza-vazquez, et al. (1995) *Plant Cell Reports* 14:482–487) and aroA (U.S. Pat. No. 5,094,945) for glyphosate tolerance, bromoxynil nitrilase (Bxn) for Bromoxynil tolerance (U.S. Pat. No. 4,810,648), phytoene desaturase (crtI (Misawa et al, (1993) *Plant Journal* 4:833–840, and (1994) *Plant Jour* 6:481–489) for tolerance to norflurazon, acetohydroxyacid synthase (AHAS (Sathasiivan et al. (1990) *Nucl. Acids Res.* 18:2188–2193)) and the bar gene for tolerance to glufosinate (DeBlock, et al. (1987) *EMBO J.* 6:2513–2519.

It should be noted that the expression constructs of the present invention may also include sequences encoding genes involved in other stress tolerance genes, for example insect or disease resistance/tolerance genes. Such insect tolerance genes are known in the art, for example the *Bacillus thuringensis* cry1Ac protein.

In addition, the expression constructs also find use in directing the production of human biological proteins (pharmaceutical proteins) from the plant plastid. Nucleic acid sequences encoding for the Human Growth Hormone (hGH) may be employed in the plastid expression constructs of the present invention.

Another example of utilizing the expression constructs of the present invention for the production of human biological proteins is the production of aprotinin.

Other sequences which may find use in the production of human biologics include sequences encoding for insulin or insulin precursors may find use in the expression constructs of the present invention. The skilled artisan will recognize that many nucleotide sequences encoding for human biologics may be employed in the constructs of the present invention to direct their expression from a plant plastid such as those described in Goodman and Gelman (1990) Pharmacological Basis of Therapeutics, Pergaman Press, 8th Edition, Sections 14 and 15.

Constructs may be prepared as to regulate the transcription and/or transcription and translation (expression) of a DNA sequence of interest from the plant cell plastid. Such constructs are known in the art and are described in U.S. Pat. No. 5,576,198, the entirety of which is incorporated herein by reference.

To direct the transcription and/or transcription and translation (expression) of a DNA sequence of interest from a plastid in the tuber of a plant, promoters providing for enhanced expression in a tuber are employed to direct the expression of T7 RNA polymerase from the plant cell nucleus. Sequences are also included to direct the RNA polymerase to the plant cell plastid. In such cases, promoters from patatin (Twell et al. (1987) *Plant Mol. Biol.* 9:365–375), zein or plant starch synthase (Visser et al. (1989) *Plant Sci.* 64:185–192) may be particularly useful for nuclear expression of a viral single subunit RNA polymerase.

Such constructs find use in the modification of starch composition in a plant cell within a plant tuber. DNA sequences which find use in such constructs include those involved in starch modification. Such DNA sequences are known in the art, and include, but are not limited to sucrose phosphate synthase (SPS, Worrell, et al. (1991) *Plant Cell* 3:1121–1130), acid invertase (Klann, et al. (1992) *Plant Physiol.* 99:351–353), glgA, glgB, and glgC (U.S. Pat. No. 5,349,123).

The invention now being generally described, it will be more readily understood by reference to the following examples which are included for purposes of illustration only and are not intended to limit the present invention.

EXAMPLES

Example 1

Construction of Vectors

Constructs and methods for use in transforming the plastids of higher plants are described in Zoubenko et al. (*Nuc Acid Res* (1994) 22(19):3819–3824), Svab et al. (*Proc. Natl. Acad. Sci.* (1990) 87:8526–8530 and *Proc. Natl. Acad. Sci.* (1993) 90:913–917), Staub et al. (*EMBO J.* (1993) 12:601–606) and in U.S. Pat. No. 5,576,198. The complete DNA sequences of the plastid genome of tobacco are reported by Shinozaki et al. (*EMBO J.* (1986) 5:2043–2049). All plastid DNA references in the following description are to the nucleotide number from tobacco.

Constructs are prepared to direct the expression of the T7 RNA polymerase in petunia. A construct pCGN6048, containing the same elements as the plasmid PCGN4026 (McBride, et al. (1994) *Proc. Natl. Acad. Sci. USA* 91:7301–7305, and U.S. Pat. No. 5,576,198), except the 35S promoter is replaced with the D8 promoter (Holton, T. A., (1992) PhD dissertation, University of Melbourne) as a Hind III/Bam HI fragment. Thus, the nuclear transformation construct, pCGN6048 (FIG. 1) contains the T7 RNA polymerase coding sequence targeted to the chloroplast using the RuBisCo small subunit (ssu) chloroplast transit peptide, driven by the D8 promoter.

Binary constructs for nuclear expression are transformed into cells of an appropriate Agrobacterium strain, such as LBA4404 (Ooms et al. (1982) *Plasmid* 7:15–29) or EHA101 (Hood et al. (1986) *J. Bacteriol.* 168:1291–1301) as per the method of Holsters et al. (*Mol. Gen. Genet.* (1978) 163:181–187) for use in preparation of transgenic plants.

A series of transformation vectors are prepared to direct the integration and expression of reporter and marker genes from the plant plastid.

The construct pCGN4276 for the expression of GUS in a plant cell plastid is as described in McBride, et al. (1994) *Proc. Natl. Acad. Sci. USA* 91:7301–7305, and in U.S. Pat. No. 5,576,198, the entirety of which is incorporated herein by reference. The construct pCGN4276 contains an expression Id cassette comprising the T7 5'/GUS/psbA 3':T7 3' expression construct cloned into a HindIII/PstI digested vector designed for integration of chimeric genes into the tobacco plastid genome by homologous recombination.

Figure 2:
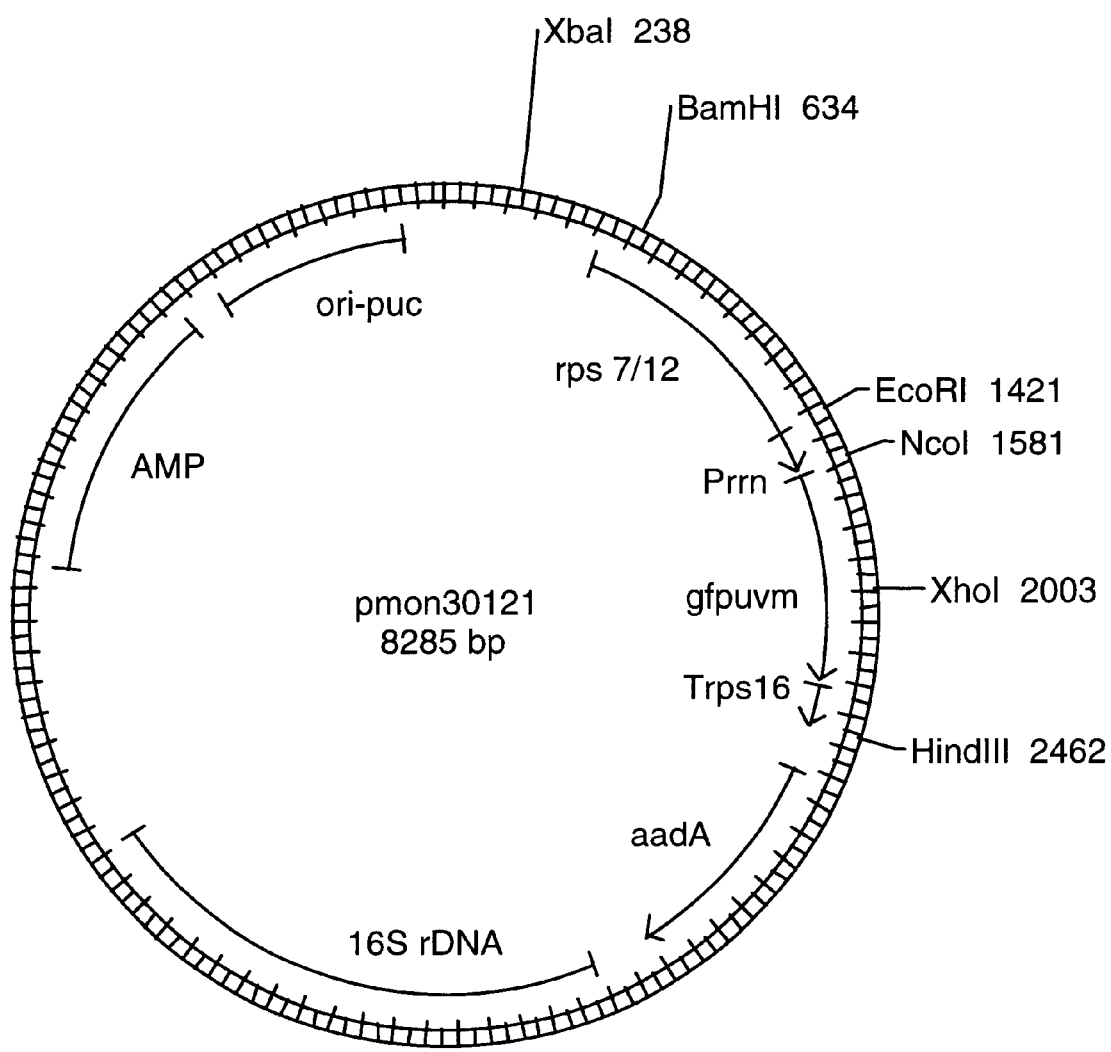
FIG. 2 provides a schematic representation of the plastid expression vector pMON30121.

An expression construct, pMON30121 (FIG. 2), was prepared to direct the integration and expression of a mutated green fluorescence protein (GFP-1) reporter gene and the aadA selectable marker gene from the plant plastid.

The GFP-1 coding sequence was derived from GFP (Clonetech) by modification by the addition of three cycle mutations (F100S, M154T, and V164A; Crameri, et al. (1996) *Nature Biotechnology* 14:315–319) and two other mutations (I167T and S175G; Haseloff, et al. (1996) *Current Biology* 6:1653–1663) to enhance GFP protein activity. The GFP-1 coding sequence was translationally fused to 7 N-terminal amino acids of the plastid rbcL gene and the rps16 transcriptional termination sequence (Trps16). This fusion is expressed from the promoter of the 16S ribosomal RNA operon (Prrn) and has a synthetic ribosome binding site.

The pMON30121 also contains the selectable marker gene, aadA (Svab and Maliga, (1993) *Proc. Natl. Acad. Sci. USA* 90:913–917) expressed from the promoter and transcriptional termination sequences of the psbA plastid gene (Svab, et al. (1993) *Proc. Natl. Acad. Sci, U.S.A.* 90:913–917).

Figure 3:
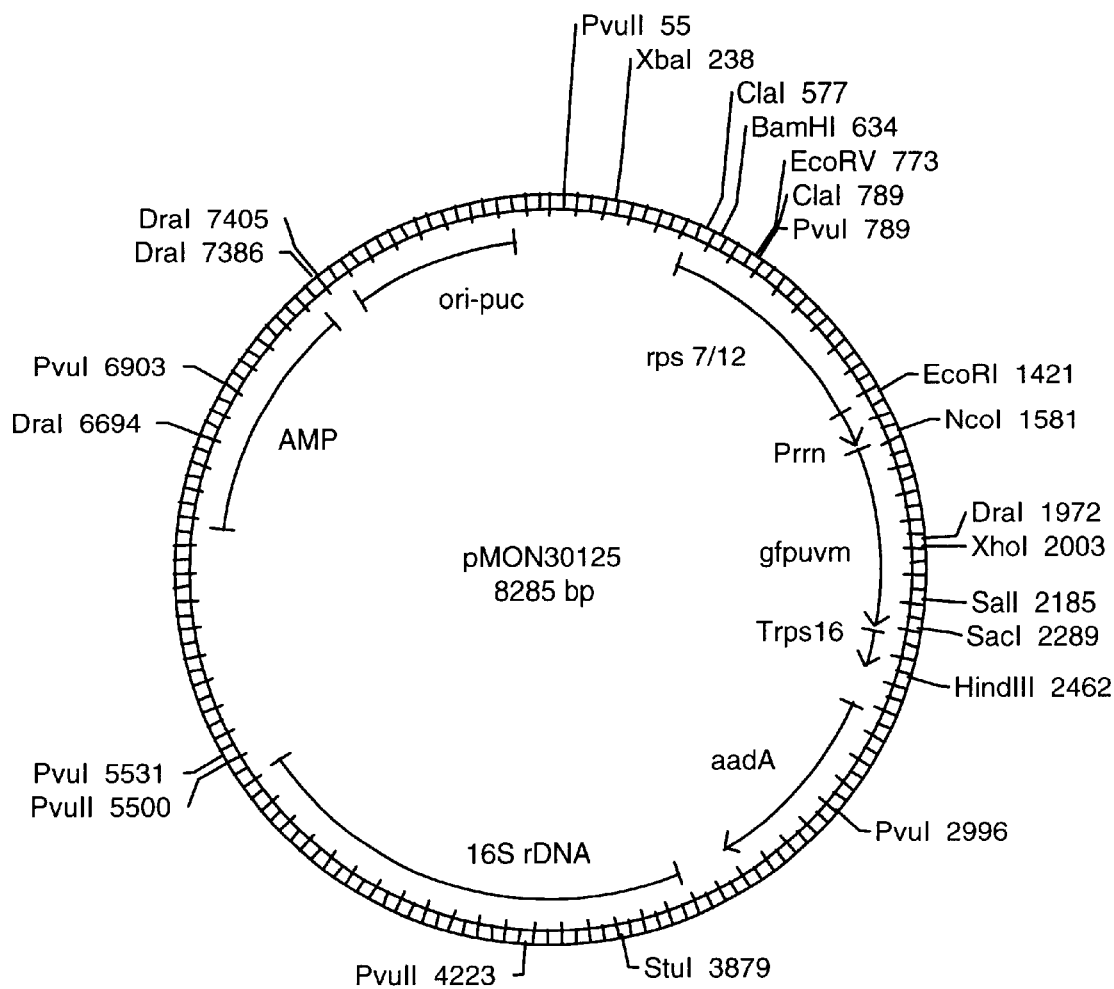
FIG. 3 provides a schematic representation of the plastid expression vector pMON30125.

An expression construct, pMON30125 (FIG. 3), was prepared to direct the integration and expression of a second mutated GFP (GFP-2)reporter gene and the aadA selectable marker gene from the plant plastid.

The GFP-2 was derived from the GFP-1 by two additional mutations (F64L and S65T, Cormack, et al., (1996) *Gene* 173:33–38). Such mutations shift the excitation wavelength to blue light. The GFP-2 gene was cloned between the Prrn/rbcL promoter/ribosome binding site and Trps16 transcription termination sequence. The Prrn/rbcL sequence is as described in Svab et al. (1993, supra). The Trps16 fragment comprises the rps16 gene 3'-regulatory region from nucleotides 5,087 to 4,939 in the tobacco plasmid DNA.

The expression cassette pMON30125 contains a marker gene, aadA, for selection on spectinomycin and streptomycin, and rps 7/12 for the integration, by homologous recombination, of the passenger DNA into trnV-rps7/12 intergenic region. The aadA marker gene is expressed from the psbA promoter and transcriptional termination sequences. The promoter region of the plastid psbA promoter (PpsbA) and terminator sequences (TpsbA) are described in Staub et al. (1993, *EMBO J.*, 12, 601–606).

Example 2

Chloroplast Transformation

2A. Tobacco Plastid Transformation

Tobacco plastids are transformed by particle gun delivery of microprojectiles as described here.

Dark green, round leaves are cut, preferably from the middle of the shoots, from 3–6 week old Nicotiana tabacum cv. Havana which have been maintained in vitro on hormone free MS medium (Murashige and Skoog, (1962) *Physiol Plant.* 15, 473–497) supplemented with B5 vitamins in Phytatrays or sundae cups with a 16 hour photoperiod at 24° C. Each cut leaf is then placed adaxial side up on sterile filter paper over tobacco shoot regeneration medium (TSO medium: MS salts, 1 mg/l $N^6$-benzyladenine, 0.1 mg/l 1-naphthaleneacetic acid, 1 mg/l thiamine, 100 mg/l inositol, 7 g/l agar pH 5.8 and 30 g/l sucrose). Leaves are preferably placed in the center of the plate with as much contact with the medium as possible. The plates are preferably prepared immediately prior to use, but may be prepared up to a day before transformation by particle bombardment by wrapping in plastic bags and storing at 24° C. overnight.

Tungsten or gold particles are sterilized for use as microcarriers in bombardment experiments. Particles (50 mg) are sterilized with 1 ml of 100% ethanol, and stored at −20° C. or −80° C. Immediately prior to use, particles are sedimented by centrifugation, washed with 2 to 3 washes of 1 ml sterile deionised distilled water, vortexed and centrifuged between each wash. Washed particles are resuspended in 500 µl 50% glycerol.

Sterilized particles are coated with DNA for transformation. Twenty-five microliter aliquots of sterilized particles are added to a 1.5 ml microfuge tube, and 5 µg of DNA of interest is added and mix by tapping. Thirty-five microliters of a freshly prepared solution of 1.8M $CaCl_2$ and 30 mM spermidine is added to the particle/DNA mixture, mixed gently, and incubated at room temperature for 20 minutes. The coated particles are sedimented by centrifuging briefly. The particles are washed twice by adding 200µl 70% ethanol, mixing gently, and centifuging briefly. The coated particles are resuspended in 50µl of 100% ethanol and mixed gently. Five to ten microliters of coated particles are used for each bombardment.

Transformation by particle bombardment is carried out using the PDS 1000 Helium gun (Bio Rad, Richmond, Calif.) using a modified protocol described by the manufacturer.

Plates containing the leaf samples are placed on the second shelf from the bottom of the vacuum chamber and bombarded using the 1100 p.s.i. rupture disk. After bombardment, petriplates containing the leaf samples are wrapped in plastic bags and incubated at 24° C. for 48 hours.

After incubation, bombarded leaves are cut into approximately 0.5 $cm^2$ pieces and placed abaxial side up on TSO medium supplemented with 500 µg/ml spectinomycin. After 3 to 4 weeks on the selection medium, small, green spectinomycin resistant shoots will appear on the leaf tissue. These shoots will continue to grow on spectinomycin containing medium and are referred to as primary putative transformants.

When the primary putative transformants have developed 2 to 3 leaves, 2 small pieces (approximately 0.5 $cm^2$) are cut from each leaf and used for either selection or for a second round of shoot regeneration. One piece is placed abaxial side up on plates containing TSO medium supplemented with 500 µg/ml spectinomycin, and the other piece is placed abaxial side up on TSO medium supplemented with 500 µg/ml each of spectinomycin and streptomycin. Positive transformants are identified as the shoots which form green callus on the TSO medium containing spectinomycin and streptomycin.

After 3 to 4 weeks, the tissue placed on TSO medium containing only spectinomycin, which has been identified as positive on the TSO medium with spectinomycin and streptomycin, will develop green shoots. Two to four shoots of each positive transformant are selected and transferred to TSO medium supplemented with 500 µg/ml spectinomycin for generation of roots. Southern analysis is performed on 2 shoots to confirm homoplasmy as described below. Shoots from homoplasmic events are transferred to the greenhouse for seed production, while transformants which are not homoplasmic are sent through a second round or regeneration on TSO medium with 500 µg/ml spectinomycin to attain homoplasmy.

2B. Potato Plastid Transformation

Potato plastids are transformed by particle gun delivery of microprojectiles as described here.

Fully expanded, dark green leaves are cut, preferably from the top of the shoots, from 2–4 week old Solanum tuberosum genotypes FL1607 and Desiree which have been maintained in vitro on hormone free MS medium (Murashige and Skoog, (1962) *Physiol Plant.* 15, 473–497) supplemented with B5 vitamins in Phytatrays or sundae cups with a 16 hour photoperiod at 16° to 22° C. Each cut leaf is then placed adaxial side up on solid MS medium supplemented with B5 vitamins and 0.2 to 0.4 M mannitol or MS medium with B5 vitamins and supplemented with 5 mg/l Zeatin Riboside (Zeatin) and 0.1 mg/l α-Naphtaleneacetic acid. Leaves are preferably placed in the center of the plate with as much contact with the medium as possible. The whole leaf surface is gently wounded with sandpaper before being placed on the shooting medium. The plates are preferably prepared 1 to 4 hours before transformation by particle bombardment.

Tungsten or gold particles are sterilized for use as microcarriers in bombardment experiments as described above.

Sterilized particles are coated with DNA for transformation. Fifty micoliter aliquots of sterilized particles are added to a 1.5 ml microfuge tube, and 10 µg of DNA of interest is added and mix by tapping. Seventy microliters of a freshly prepared solution of 1.8M $CaCl_2$ and 30 mM spermidine is added to the particle/DNA mixture, mixed gently, and incubated at room temperature for 20 minutes. The coated particles are sedimented by centrifuging briefly. The particles are washed twice by adding 200 µl 70% ethanol, mixing gently, and centifuging briefly. The coated particles are resuspended in 160 µl of 100% ethanol and mixed gently. Eight to fifteen microliters of coated particles are placed in the center of the macrocarrier and allowed to dry in a low humidity environment, preferably with a desiccant.

Transformation by particle bombardment is carried out using the PDS 1000 Helium gun (Bio Rad, Richmond, Calif.) using a modified protocol described by the manufacturer.

Plates containing the wounded leaf samples are placed on the second shelf from the bottom of the vacuum chamber and bombarded using the 1100 p.s.i. rupture disk. After the initial bombardment, the plates are moved to the first from the bottom shelf and bombarded a second time using a 1350 p.s.i. rupture disk. After bombardment, the leaves are transferred to petriplates with liquid Z1 medium (MS medium with B5 vitamins plus 5 mg/l Zeatin or 5 mg/l Zeatin and 0.1 mg/l α-Naphtaleneacetic acid (NAA)). Preferably, 5–8 leaves are transferred into each plate with 5 Whatman filter papers (size 8.5 cm) and 10 ml of Z1 medium. The plates are a incubated for 3 days under 16 hour light period at 20° C. to 25° C. (Delay period)

After the delay period, bombarded leaves are cut into approximately 0.25–0.5 $cm^2$ pieces and placed adaxial side up on solid Z1 medium supplemented with 300 mg/l spectinomycin. After 4 to 9 weeks on the selection medium, small, green spectinomycin resistant calli will appear on the leaf tissue. The green calli are subcultures to the same medium, except supplemented with 40 mg/l spectinomycin for shoot regeneration. Regenerated shoots are transferred to MS medium, without hormones (I.e. hormone free medium) with 40 mg/l spectinomycin. These shoots will continue to grow on spectinomycin containing medium and are referred to as primary putative transformants.

When the primary putative transformants have developed 3 to 5 leaves, nodal cuttings from each event are checked for growth on MS medium with 500–1000 mg/l streptomycin. If the primary shoot is a true transformant, the shoots will grow and form roots. Positive transplastomic events can be checked for fluorescence by GFP. PCR or Southern blot hybridizations may be performed to confirm chloroplast transformation.

Figure 4:
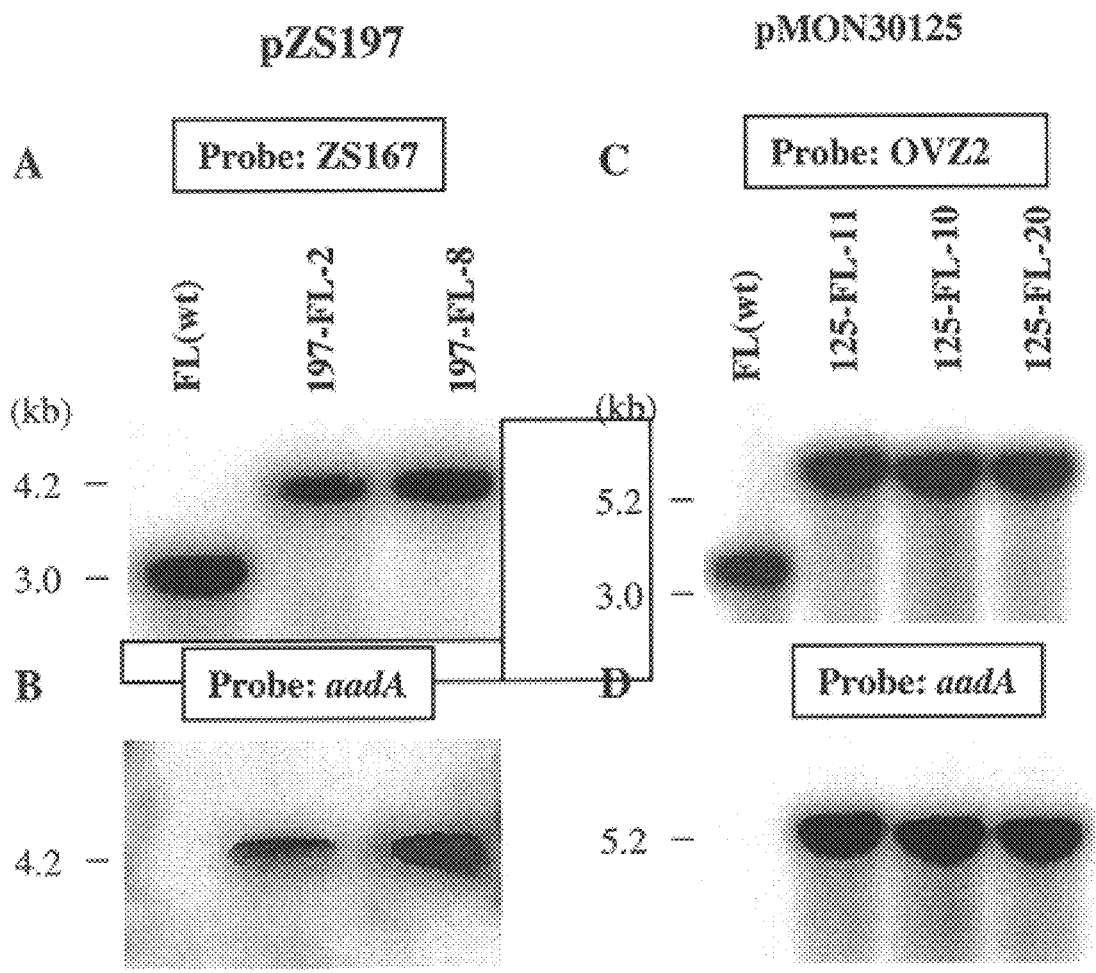
FIGS. 4A–4D provide the results of Southern analysis of independent transplastomic potato events obtained after transformation with pMON30125. Total cellular DNA isolated from nontransformed potato leaves FL(wt), and from leaves of transformed plants (125-FL-11, 125-FL-10, 125-FL-20) was digested with BamHI for pMON30125 derived transformants. The blots were probed with (A) 2.4 Kb EcoRI/EcoRV ptDNA fragment from pZS197 and (B) the 0.8 kb aadA coding region.

Total cellular DNA was extracted by the method of Mettler ((1987) *Plant Mol. Biol. Reporter* 5:346–349). The DNA was digested with BamHI for pMON30125 derived transformants. DNA was electrophoresed on a 0.8% agarose gel and then transferred to nylon membrane (Amersham) using the Posiblot apparatus (Stratagene). Radioactively labeled probes were generated by random priming (Boehringer Mannheim)of the 0.8 kb aadA coding region and the 2.4 Kb EcoRI/EcoRV fragment from pZS167 (Svab, et al (1993) supra). DNA gel blots were hybridized at 65C in Rapid Hybridization Buffer (Amersham). After hybridization overnight at 65C, blots were washed in 0.1%SSPE plus 0.1%SDS and then exposed to x-ray film. The results of Southern hybridization are shown in FIG. 4.

Three lines (125-FL-10, 125-FL-11 and 125-FL-20) are identified as containing GFP, and pure, homoplasmic, lines are obtained after several rounds of subculturing on media containing 300 mg/ml spectinomycin.

2C. Petunia Plastid Transformation

Petunia plastids are transformed by particle gun delivery of microprojectiles as described here.

Fully expanded petunia leaves (var. mitchell) from plants grown in tissue culture are excised and placed abaxial surface up on a Whatman #1 filter paper in PRMOP media (1×MS Salts, 1×B5 vitamins, 1 mg/l 6-Benzylaminopurine (BAP), 0.1 mg/l NAA, 30 g/l sucrose) for bombardment.

Tungsten or gold particles are sterilized for use as microcarriers in bombardment experiments as described above.

Sterilized particles are coated with pCGN4276 vector DNA for transformation. Ten ug of DNA is precipitated onto 2.5 mg tungsten particles using 50 ul 2.5 M CaCl2 and 20 ul 0.1 M spermidine free base, and vortexing for 20 min. After vortexing the particles are washed 4 times in 100% ethanol and resuspended in 100% ethanol. After bombardment the leaves are left on the filter paper media for a two (2) day delay period at a 12 hour photoperiod at 24° C.

After the delay period, the bombarded leaves are cut into 5 mm pieces and placed on PRMOP media with 500 mg/l spectinomycin dihydrochloride. The leaves are left to regenerate on PRMOP media for 2 months. The BAP level in the media is doubled to 2 mg/l and the callus is allowed to grow for 2 additional months to produce shoots. The shoots obtained contained transformed plastids and are fertile.

2D. Alternative Petunia Plastid Transformation Protocol

Alternatively, petunia leaf tissue prepared and bombarded as above may be cultured and regenerated on PRMOP media containing 3 mg/l BAP. By increasing the amount of BAP in the PRMOP media, a greater number of regenerated petunia shoots are obtained.

Furthermore, concentrations of spectinomycin are altered to increase the number of transformed petunia shoots. By decreasing the amount of spectinomycin to 250 mg/l during culturing and regeneration, a greater number of plant shoots are obtained. Furthermore, by culturing on RMOP media containing high levels of spectinomycin (500 mg/l to 1000 mg/l), then removing the spectinomycin or lowering the spectinomycin levels during regeneration, an increased number of regenerated shoots is observed.

Example 3

Transplastomic Tobacco Plant Analysis

3A. Western Immunoblot Analysis

Transplastomic tobacco lines containing pMON30121 or pMON30125 were analyzed for GFP expression. Three 30121 lines and seven 30125 lines were identified for further analysis.

To determine the expression of GFP from the tobacco plastid, Western immunoblot analysis was performed on lines from each construct, pMON30121 and pMON30125.

Total soluble protein was extracted from frozen leaf tissue by grinding 250 mg tissue in 250µl of PBS buffer (1 mM $KH_2PO_4$, $Na_2HPO_4$, 0.137M NaCl, 2.7 mM KCl pH 7.0) containing protease inhibitors. The homogenate is centrifuged for 5 minutes, and the supernatant is transferred to a fresh tube. The concentration of the protein in the supernatant is determined using a protein concentration assay (BioRad, Richmond, Calif.).

Extracted total protein is electrophoresed on a 4–20% SDS-PAGE gel (Sigma, St Louis, Mo.), and transferred to PVDF membrane in 1×SDS-PAGE buffer (Maniatis et al. 1989, Cold Spring Harbor Press). Standards of quantitated purified CP4 EPSPS protein were used to quantify the expression of the CP4 EPSPS as expressed in the plant plastid.

Western hybridizations are performed as described in Staub and Maliga (1993) *EMBO Journal*, 12(2) 601–606, except using antibodies raised to EPSPS. PVDF membranes containing the transferred electrophoresed protein were incubated in a blocking solution of PBS buffer containing 0.05% Tween-20 (PBS-T) and 5% milk overnight at 4° C. The membranes are then incubated in a solution of PBS-T containing 1% milk and a primary antibody raised in goats to GFP for 2 hours at room temperature. The membranes are washed three times in a solution of PBS-T containing 0.1% milk, each wash for 5 minutes at room temperature. The membranes are then incubated in a solution of PBS-T containing 1% milk and sheep anti-goat antibody for 1 hour at room temperature, and washed again in PBS-T containing 0.1% milk, three times for 10 minutes at room temperature. A final wash using only PBS-T is performed before developing the membranes using a nonradioactive detection kit (ECL, Amersham).

TABLE 1

| Construct Number | Event Number | % Total Soluble Protein |
| --- | --- | --- |
| pMON30121 | 22-1 | 4 . 5% |
| pMON30121 | 40-1 | 4–5% |
| pMON30125 | 46-3 | 4–5% |
| pMON30125 | 43-1 | 4–5% |

The results listed in Table 1 demonstrate that significant levels of GFP are expressed from the tobacco plant plastid. Total soluble protein levels were estimated from the Western blot analyses.

3B. Visual Observation of GFP Expression

To visually observe the expression of GFP from the chloroplasts of transformed plants, various tissues are visualized utilizing a dissecting microscope. Protoplasts and chloroplasts are isolated as described in Sidorov, et al. (1994) *Theor. Appl. Genet.* 88:525–529.

Analysis of putative transgenic is carried out using a dissecting microscope Leica MZ-8 with GFP Plus Fluorescence module # 10446143. Freshly prepared protoplasts, leaf epidermis, isolated chloroplasts are examined under blue and UV light using compound fluorescence microscope III-RS (Zeiss) and inverted microscope Axiovert 100S (Zeiss). Images are taken on Fujichrome ISO 1600 film. The results of the observations are shown in Table 2.

TABLE 2

| TISSUE | GFP EXPRESSION |
| --- | --- |
| Leaf | yes |
| Stem | yes |
| Root | yes |
| Anther | yes |
| Filament | yes |
| Mature Pollen | Strong Autofluorescence |
| Microspore | No |
| Style | yes |
| Ovary | yes |
| Ovule | yes |
| Epidermal cells | yes |
| Stomata cells | yes |
| Trichomes | yes |

Results of the visual observations demonstrates that GFP expressed from the plastid is expressed in most plant tissues tested. GFP expression was difficult to detect in the mature pollen due to the strong autofluorescence of the pollen under blue light.

Example 4

Transplastomic Potato Plant Analysis

Three transplastomic potato lines were visually inspected for GFP expression as described above. The results are shown in Table 3 below.

TABLE 3

| TISSUE | GFP EXPRESSION |
| --- | --- |
| Leaf | Yes |
| Stem | Yes |
| Root | Yes |
| Epidermal Cells | Yes |
| Stomata Cells | Yes |
| Trichomes | Yes |

Similar to the tobacco transformation, results of the visual observations in potato shows that the GFP protein is expressed in all potato tissues examined. In addition, the a visual observations confirm that the cells contain a pure population of plastids (homoplasmic).

Western Immunoblot analysis is performed to determine the level of GFP expression in transplastomic potato lines. Total cell protein was extracted in ice cold Phosphate buffered saline solution containing 1× Proteinase inhibitor cocktail (Boehringer Mannheim). After centrifugation at 4C for 10 min. to remove cell debris, soluble protein extract was collected and protein concentrations were determined using the Bio-Rad protein assay reagent kit. 0.5 mg of total cellular protein (leaf) or 10 ug (microtubers) protein extracts are electrophoresed on 4–20% gradient SDS-PAGE gels (Sigma) and transferred to Immobilon-P membrane (Millipore) using a semi-dry transfer apparatus (integrated Separation Systems). Immunoblot detection used ECL chemiluminescence and 1:3000 diluted HRP-conjugated secondary antibody (Sigma). Purified protein used as control and polyclonal antiserum (1:1000 working dilution) to Green Fluorescent Protein (GFP) was purchased from Biodesign. GFP was quantified on the immunoblots by comparison of experimental samples to a dilution series of the purified GFP protein.

Figure 7:
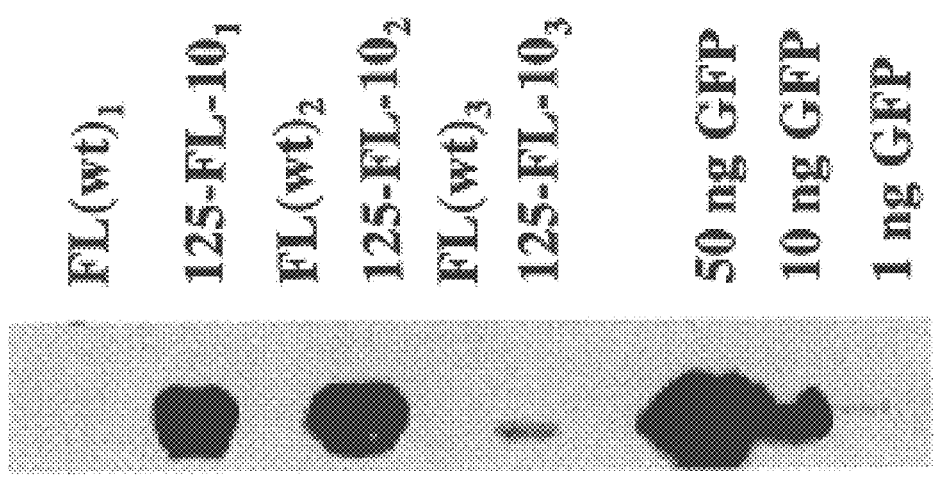
FIG. 7 provides the results of immunoblot analysis of GFP accumulation in leaves and microtubers of transformant line 125-FL-10. GFP standards (50, 10, 1 ng) are included. FL(wt)1, FL(wt)2, FL(wt)3: extracts from leaves of greenhouse and in vitro plants and microtubers of control FL line, respectively. 125-FL-101, 125-FL-102, 125-FL-103: extracts from leaves of greenhouse and in vitro plants and microtubers of transgenic line 125-FL-10.

The level of GFP expression is examined in leaves of in vitro plants and green house grown plants and also in microtubers induced in vitro. The results demonstrate that green fluorescent protein accumulated at highest concentration in leaves of greenhouse grown plants. Also by comparison to standard GFP it is found that leaves of transgenic potato plants accumulate about 5% of their total protein as GFP. At the same time tuber tissue had approximately 0.05% GFP (FIG. 7).

Example 5

Transplastomic Petunia Plant Analysis

Figure 5A:
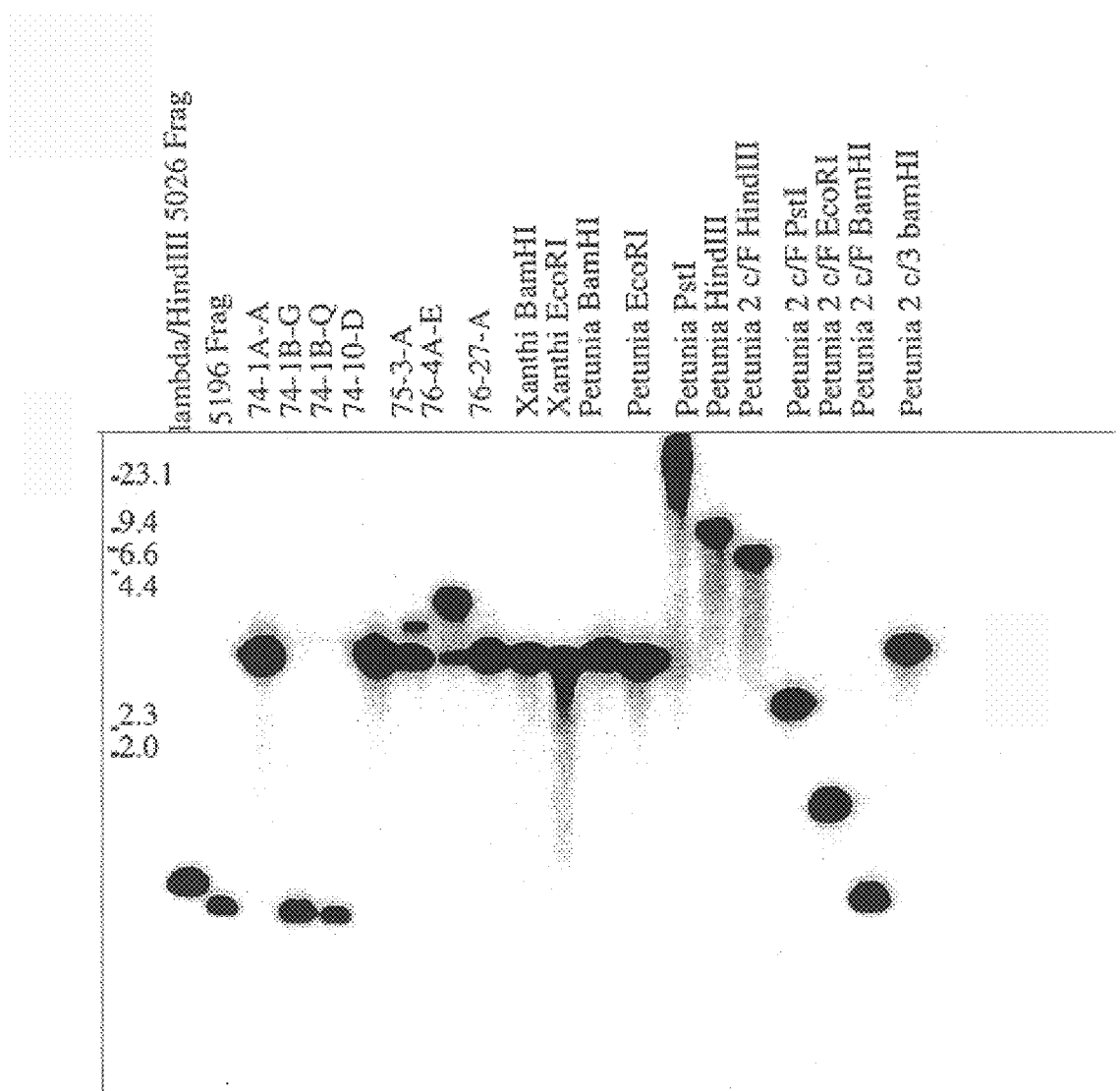
FIGS. 5A–5B provide the results of the Southern blot analysis of independent transplastomic petunia events obtained after transformation with pCGN4276. Total cellular DNA isolated from the leaves of nontransformed petunia variety Mitchell(wt) and transformed plants (line 2) was digested with various endonucleases. The blots were probed with (A) BamHI fragment from pOZV44b and (B) the 0.83 kb aadA coding region.
Figure 5B:
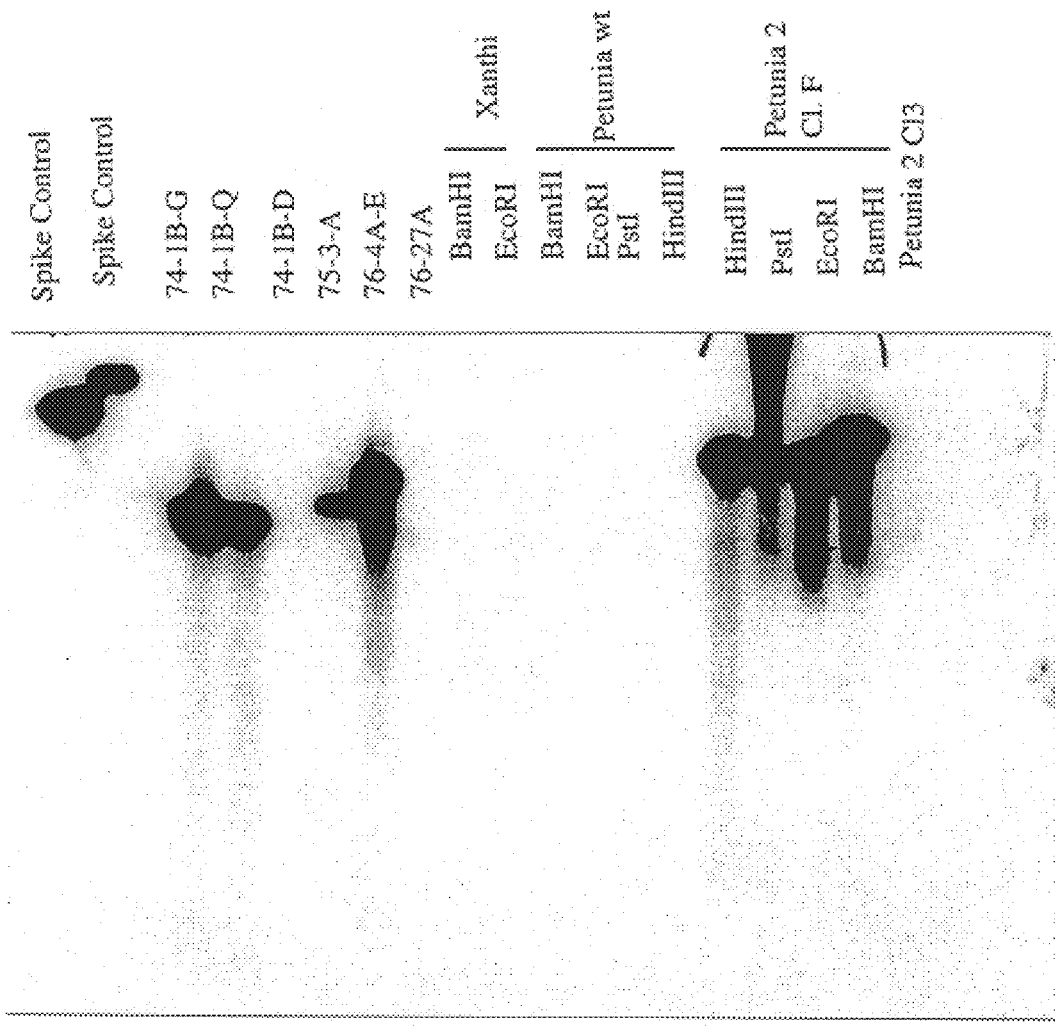

Following plastid transformation as described above for petunia, two independently isolated homoplasmic lines are generated and designated as 4276 clones 1 and 2. Homoplasmy was demonstrated by Southern blot analysis as shown in FIG. 5.

Total plant cellular DNA is prepared as described by Dellaporta et al. (1983) Plant Mol. Biol. Rep. 1:19–21). Approximately 3 µg DNA for each sample is digested with various restriction endonucleases, electrophoresed through 1% agarose, transferred to Nytran+ and the filters hybridized with alpha $^{32}$P-dCTP labeled probe. Probe A (FIG. 5A) demonstrates degree of transformation (homoplasmy) and probe B (FIG. 5B) reveals presence of the aadA gene. Hybridization with probe A demonstrates that the introduction of a new BamHI site from the transgene changes the size of the probed fragment from 3.3 kb to about 0.6 kb in the transplastomic lines.

Two petunia lines derived from a single transplastomic plant were identified as homoplasmic and containing the aadA selectable marker. These two lines, also referred to as subclones, are referred to as lines 2+B and 2+D.

The two lines generated, 2+B and 2+D, are used as explant sources for nuclear transformation experiments. Two transplastomic 4276 petunia lines, as well as two control lines, are transformed with pCGN6048.

Transgenic petunia plants are obtained by Agrobacterium-mediated transformation as described by Horsch et al. (Science (1985) 227:1229–1232).

Figure 6:
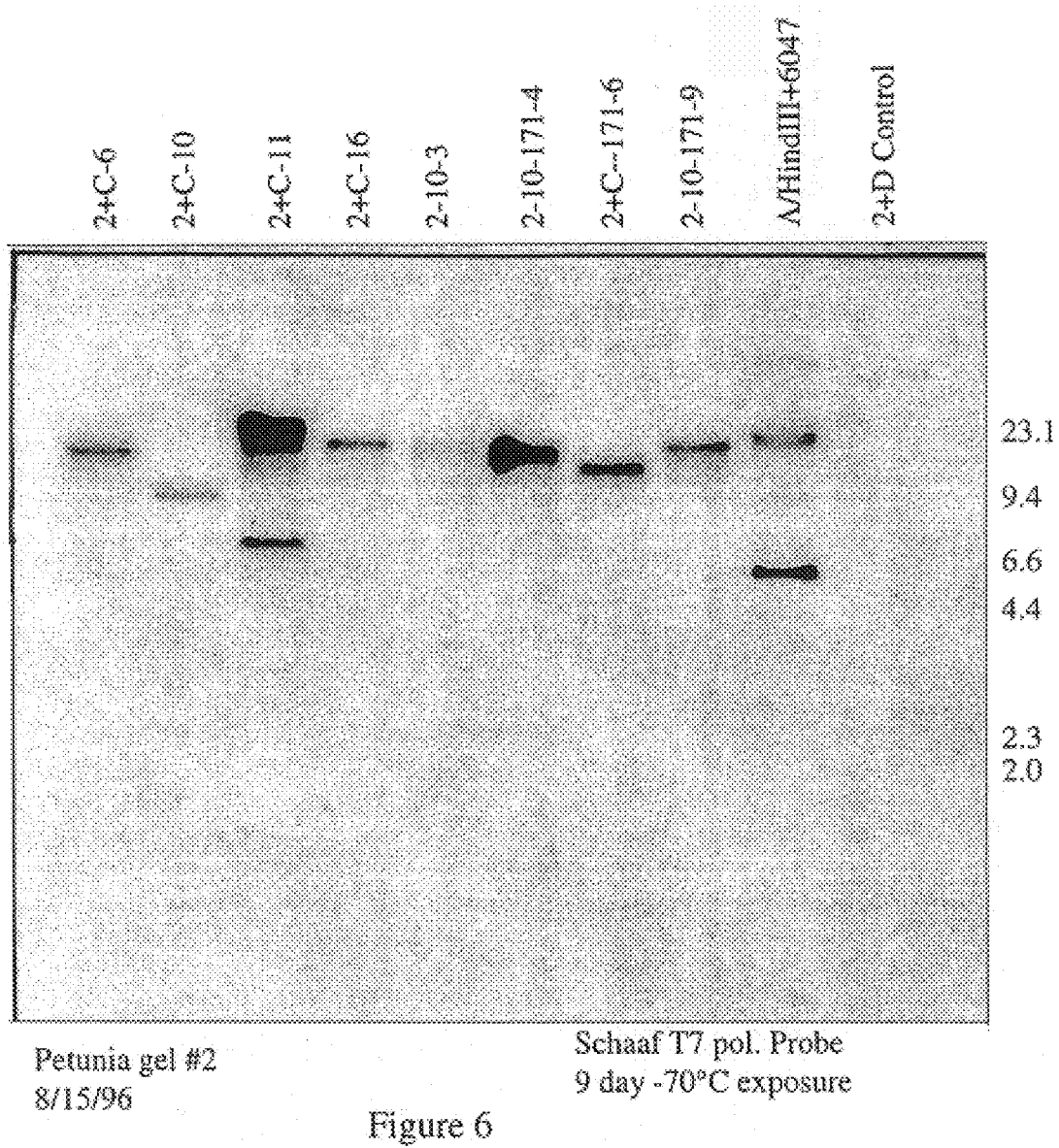
FIG. 6 provides the results of the Southern blot analysis of independent transgenic petunia events obtained after transformation of lines containing pCGN4276 with pCGN6048. Total cellular DNA isolated from the leaves of nontransformed petunia variety Mitchell(wt) and transformed plants (line 2) was digested with various endonucleases. The blots were probed with a DNA sequence encoding for the T7 polymerase gene.

Plants which regenerated on media containing kanamycin are analyzed using Southern blot hybridizations to determine the presence of the T7 polymerase DNA sequence (FIG. 6).

To demonstrate that the T7 GUS transcripts are translated in the transgenic plastids, β-glucuronidase specific activity was measured in various tissues. GUS assays are conducted as described by Jefferson et al. (EMBO J. (1987) 6:3901–3907) using a Dynaquant 200 Fluorometer (Hoefer). The results of these assays in various tissues from a 4276/6048 clone are shown below in Table 4.

TABLE 4

| | nmol Mu/min/mg | | | |
| --- | --- | --- | --- | --- |
| LINE | LEAF | PETAL | NEW PETAL | SENESCENT PETALS |
| Mitchell 2–10 | 311 | 285 | 316 | 5,350 |
| 2 + C | 1,583 | 455 | 283 | 4,073 |
| 2 + D | 680,303 | 637,048 | 813,388 | 2,515,000 |

Example 7

Inheritance Studies

To demonstrate that the GUS reporter gene behaves as a maternally inherited character, several crosses were conducted. Seed derived from the crosses were germinated and the seedlings scored for β-glucuronidase activity by staining with the histochemical substrate X-gluc. Crosses between transplastomic petunia lines 2+B and 2+D (containing pCGN4276) and transgenic petunia lines containing pCGN6048. The Mitchell (6048-12) and 2–10 6048-9 lines are hemizygous for T7 polymerase. The 2–10 6048-3 line is a null line co-cultivated with 6048, the line does not express the T7 polymerase. The crosses and results are shown in table 5.

TABLE 5

| PARENT | | | EXPECTED |
|---|---|---|---|
| FEMALE | MALE | RESULT | RESULT |
| Mitchell (6048-12) | × 2 + D (4276) | 2 negative | Negative |
| 2 + D (4276) | × Mitchell (6048-12) | 1 Positive, 1 Negative | Positive |
| 2 + B (4276) | × 2–10 6048-3 | 2 negative | Negative |
| 2 + D (4276) | × 2–10 6048-3 | 2 negative | Negative |
| 2 + D (4276) | × 2–10 6048-9 | 1 positive, 1 negative | Positive |
| 2 + B (4276) | × 2–10 6048-9 | 1 positive, 1 negative | Positive |

These results demonstrate that the GUS gene is inherited as a maternal trait in petunia. Thus demonstrating that the GUS expression cassette is contained in the plant cell plastid.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for transforming a plastid genome of a non-tobacco solanaceous plant cell comprising the steps of:

introducing into said non-tobacco solanaceous plant cell a construct comprising a promoter functional in a solanaceous plant cell plastid operably associated with a DNA sequence of interest and a transcriptional termination region functional in a solanaceous plant cell plastid, and said construct further comprising regions of homology to said non-tobacco plastid genome, which regions of homology arm from a tobacco plastid genome for the integration of said construct into the non-tobacco solanaceous plant cell plastid genome;

identifying non-tobacco solanaceous plant cells containing a transformed plastid genome containing said construct: and regenerating a multicellular plant from said non-tobacco solanaceous plant cells containing said transformed plastid genome.

2. The method according to claim 1 wherein said non-tobacco solanaceous plant cell is from a potato.

3. The method according to claim 2 wherein said non-tobacco solanaceous plant cell is a cell from a leaf of said potato.

4. The method according to claim 3 further comprising the step of wounding the surface of said potato leaf prior to introducing said construct into said potato leaf cell.

5. The method according to claim 1 wherein said non-tobacco solanaceous plant cell is from a petunia.

6. The method according to claim 5 wherein said non-tobacco solanaceous plant cell is a cell from a leaf of said petunia.

7. A non-tobacco solanaceous plant cell plastid obtained by the method of claim 1.

8. A non-tobacco solanaceous plant, plant seed, plant cell or progeny thereof each containing a plant cell plastid according to claim 7.

9. A non-tobacco solanaceous plant cell having a plastid genome comprising a heterologous construct integrated into said plastid genome, said construct comprised of a promoter functional in a solanaceous plant cell plastid operably associated with a DNA sequence of interest and a transcriptional termination region functional in a solanaceous plant cell plastid, and said construct further comprising regions of homology to said non-tobacco plastid genome, which regions of homology are from a tobacco plastid genome.

10. The non-tobacco solanaceous plant cell according to claim 9 wherein said non-tobacco solanaceous plant cell is a potato cell.

11. The non-tobacco solanaceous plant cell according to claim 10 wherein said potato cell comprises a leaf cell.

12. The non-tobacco solanaceous plant cell according to claim 11 wherein said potato cell comprises a tuber cell.

13. The non-tobacco solanaceous plant cell according to claim 9 wherein said non-tobacco solanaceous plant cell is a petunia cell.

14. The non-tobacco solanaceous plant cell according to claim 13 wherein said petunia cell is a leaf cell.

15. A non-tobacco solanaceous plant, plant seed, plant cell or progeny thereof each containing a plant cell according to claim 9.

* * * * *

UNITED STATES PATENT AND TRADEMARK OFFICE
CERTIFICATE OF CORRECTION

PATENT NO. : 6,541,682 B1 Page 1 of 1
APPLICATION NO. : 09/191303
DATED : April 1, 2003
INVENTOR(S) : Nehra et al.

It is certified that error appears in the above-identified patent and that said Letters Patent is hereby corrected as shown below:

In claim 1, Column 17, line 51, "arm" should read "are"

In claim 12, Column 18, line 42, "claim 11" should read "claim 10"

Signed and Sealed this

Eleventh Day of July, 2006

JON W. DUDAS
*Director of the United States Patent and Trademark Office*